United States Patent
Sun et al.

(10) Patent No.: US 6,320,388 B1
(45) Date of Patent: Nov. 20, 2001

(54) MULTIPLE CHANNEL PHOTO-IONIZATION DETECTOR FOR SIMULTANEOUS AND SELECTIVE MEASUREMENT OF VOLATILE ORGANIC COMPOUND

(75) Inventors: Hong T. Sun, Sunnyvale; Peter C. Hsi, Fremont, both of CA (US)

(73) Assignee: RAE Systems, Inc., Sunnyvale, CA (US)

( * ) Notice: Subject to any disclaimer, the term of this patent is extended or adjusted under 35 U.S.C. 154(b) by 0 days.

(21) Appl. No.: 09/330,522

(22) Filed: Jun. 11, 1999

(51) Int. Cl.[7] .............................. G01N 27/62; G01T 1/18
(52) U.S. Cl. .................. 324/464; 324/459; 250/382; 250/281; 250/289; 250/384
(58) Field of Search ..................... 324/464, 459; 250/423 R, 423 F, 281, 306, 288, 389, 374, 382

(56) References Cited

U.S. PATENT DOCUMENTS

| | | | |
|---|---|---|---|
| 4,341,049 | * 7/1982 | Hsi | 250/382 |
| 4,376,893 | * 3/1983 | Whetten | 250/374 |
| 4,429,228 | * 1/1984 | Anderson | 250/382 |
| 4,704,536 | * 11/1987 | Sugiyyama et al. | 250/381 |
| 4,778,998 | * 10/1988 | Carnahan | 250/382 |
| 5,028,544 | * 7/1991 | Rasulev et al. | 436/161 |
| 5,393,979 | * 2/1995 | Hsi | 250/382 |
| 5,431,714 | * 7/1995 | Burtscher et al. | 95/6 |
| 5,504,328 | * 4/1996 | Bonser | 250/288 |
| 5,540,898 | * 7/1996 | Davidson | 422/186.1 |
| 5,561,344 | * 10/1996 | Hsi | 313/494 |
| 5,572,137 | * 11/1996 | Jones | 324/464 |
| 5,604,059 | * 2/1997 | Imura et al. | 430/5 |
| 5,773,833 | * 6/1998 | Hsi | 250/382 |
| 5,855,850 | * 1/1999 | Sittler | 422/98 |
| 5,968,837 | * 10/1999 | Doring et al. | 436/173 |

* cited by examiner

Primary Examiner—Glenn W. Brown
Assistant Examiner—Wasseem H. Hamdan
(74) Attorney, Agent, or Firm—Skjerven Morrill MacPherson LLP; David W. Heid

(57) ABSTRACT

A multiple-channel photo-ionization detector (PID) determines the concentrations of specific gases or classes of gases. The PID includes a UV lamp, an optical window which is divided into multiple zones with each zone producing a UV light beam having a distinctive maximum photon energy. The ionization chamber of the PID includes multiple ion detectors. The PID measures ionization currents and concentrations of gases ionizable by each UV light beam. A method of determining the concentrations and/or identifications of the individual component gases uses differences and/or ratios of measured concentrations or currents.

20 Claims, 7 Drawing Sheets

MULTIPLE CHANNEL PHOTO-IONIZATION DETECTOR FOR SIMULTANEOUS AND SELECTIVE MEASUREMENT OF VOLATILE ORGANIC COMPOUND

BACKGROUND OF THE INVENTION

1. Field of the Invention

This invention relates to a volatile gas detector and particularly to a portable photo-ionization detector (PID).

2. Description of Related Art

Photo-ionization detectors (PIDS) can detect volatile gases. FIG. 1 shows a conventional portable PID 10 that includes an ultraviolet (UV) lamp 12 and an ionization chamber 14. UV lamp 12 produces UV light including UV photons having energy up to 8.4 electron volts (eV) or more. The UV photons pass through an optical window 16 into ionization chamber 14. In ionization chamber 14, the UV photons collide with and ionize volatile gas molecules having ionization potentials below the energy of the photons, creating ions and electrons.

PID 10 further includes an ion detector 18 having a pair of electrodes 20 and 22, which are typically made of a metal. Ion detector 18 has a high voltage (150 V or more) applied across electrodes 20 and 22 to generate an electrical field. In particular, electrode 22 is biased to a high voltage to attract negatively charged particles (electrons) and repel positively charged particles (ions), and electrode 20 is grounded to collect the positively charged particles (ions). The movement of the ions to electrode 22 produces a current, from which the concentration of the volatile gas can be determined. More specifically, the magnitude of the current depends on the number of ions produced from the collisions between volatile gas molecules and UV photons. Accordingly, the magnitude of the current depends on the concentration of ionizable volatile gas molecules and the intensity of UV light in ionization chamber 14. If the UV light intensity is constant, a measurement of the current directly related to the concentration of ionizable gases.

During use of PID 10, a gas sample in ionization chamber 14 can contain air mixed with one or more volatile gases that have ionization potentials lower than the maximum energy of the UV photons from UV lamp 12. PID 10, which has a single ion detector 18, measures ion current and the total concentration for the ionizable gases of all types in the sample. PID 10 cannot determine the concentrations of individual gases in the gas sample.

U.S. Pat. No. 5,393,979, which is herein incorporated by reference in its entirety, discloses a PID that includes multiple single channel PIDs that measure the concentrations of different types of gases in a gas sample. For instance, the PID may include three UV lamps having different maximum photon energies of 9.8, 10.2, and 11.7 eV and an ionization chamber including three ion detectors respectively in front of respective UV lamps. When a gas sample flows through the ionization chamber, each of the UV lamps, which are arranged in tandem, ionizes only the gases having ionization potentials below the maximum photon energy of the lamp, and the associated ion detector measures a current that the lamp generates from the gas sample. The three measured currents from the ion detectors differ from one another if the gas sample contains gases that can only be ionized by UV light from some of the lamps. The concentrations of gases having ionization potentials below each photon energy can be determined from the respective measured currents.

SUMMARY OF THE INVENTION

In accordance with an embodiment of the present invention, a PID measures the concentrations of volatile gases in a gas sample that flows through an ionization chamber of the PID. The PID includes a UV lamp having an optical window that is divided into multiple window zones. Each window zone produces UV photons having a distinctive energy distribution.

The ionization chamber includes multiple ion detectors that are in front of respective window zones of the optical window. Each ion detector measures the current generated when the UV photons from the corresponding window zone ionize the gas sample. Since the energies of UV photons passing through the optical window from the UV light vary according to the window zones through which the UV photons pass, the UV photons from different zones ionize different components of the gas sample. Accordingly, the currents measured at the ion detectors can differ from one another, and the concentrations of the various component gases can be determined from the separate current measurements.

The differentiated zones of the optical window can be formed by modifying the material characteristics of the optical window from zone to zone, changing the dimensions (e.g., thickness) of the optical window, or using different optical materials in each zone. For example, different coatings or thicknesses of the optical window transmit different wave lengths of UV light and permit selection of the photon energies to identify specific gases.

Each ion detector has a pair of electrodes. One is a bias electrode, and the other is a measurement electrode. In one embodiment of the invention, the measurement electrodes of the ion detectors are separate from one another, but the bias electrodes can be either separate or common.

Another embodiment of the invention provides a method of determining the concentrations of specific gases or classes of gases in a gas sample. The method comprises: producing a plurality of UV light beams having different spectrums; passing the UV light beams through the gas; measuring a plurality of current signals caused by the beams ionizing gas molecules; converting the current signals to concentrations of gas molecules ionizable by each beam; and determining the concentration of the selected gas compounds by finding a difference between a first concentration of gas molecules ionizable by a first UV light beam and a second concentration of gas molecules ionizable by a second UV light beam. The method can further identify the specific gases by comparing ratios of the current signals to a table of ratios associated with the gases.

DESCRIPTION OF THE PREFERRED EMBODIMENT

In accordance with an aspect of the present invention, a photo-ionization detector (PID) includes a UV lamp with an optical window that is divided into multiple window zones. Each window zone transmits UV light having a different spectrum or maximum photons energy. Hence, the zones produce UV photons of different energies. The PID further includes an ionization chamber next to the UV lamp. The ionization chamber contains multiple ion detectors, and each ion detector is close to a corresponding window zone. Accordingly, when a gas sample containing ionizable gases flows through the ionization chamber, the UV photons of different energies ionize different gas components of the gas sample, and the ion detectors measure the various currents caused when UV photons from the corresponding window zones ionize volatile gases. The different energy levels of the UV photons from different window zones ionize different volatile gases, and ionization levels vary across the ionization chamber.

Figure 1:
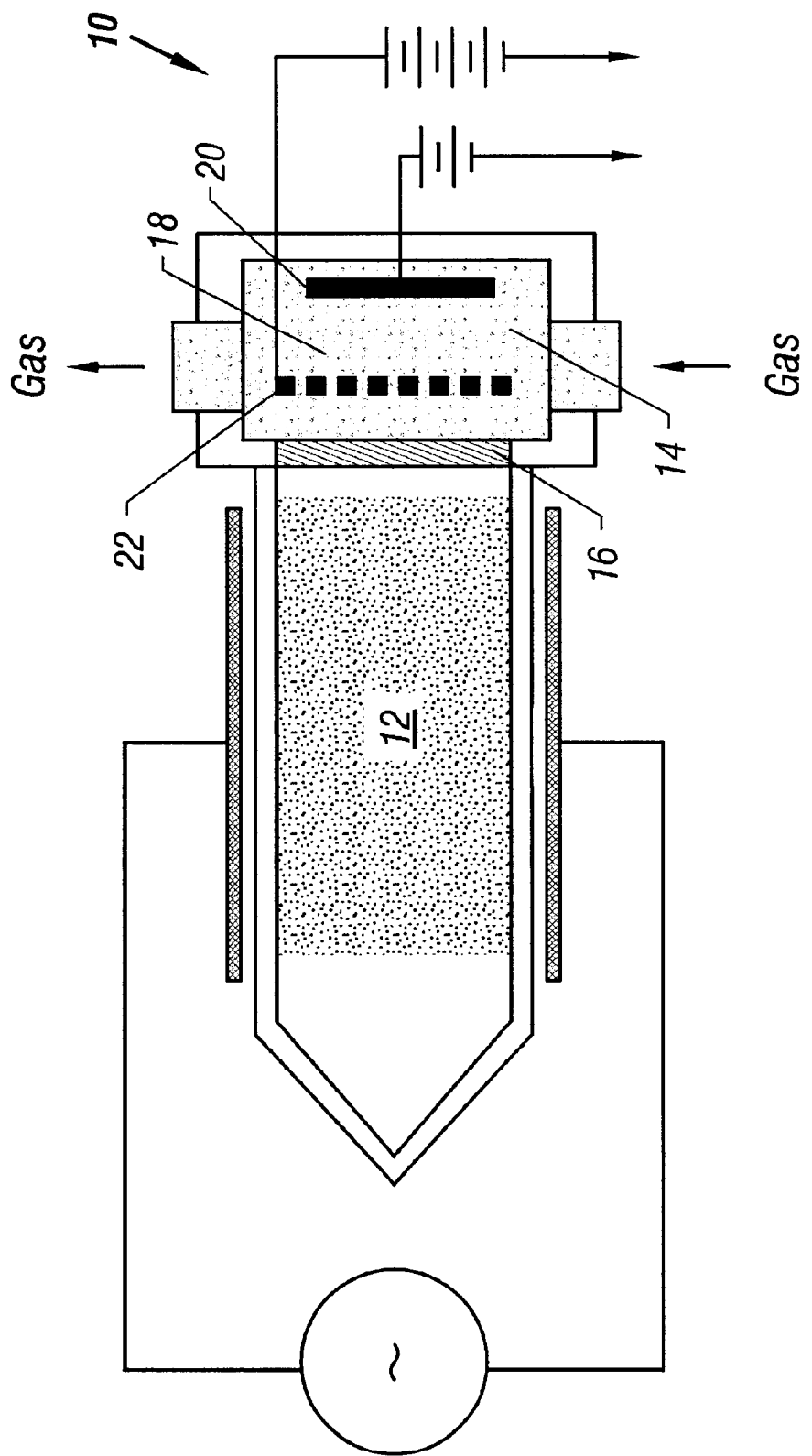
FIG. 1 is a block diagram of a conventional photo-ionization detector (PID).
Figure 2:
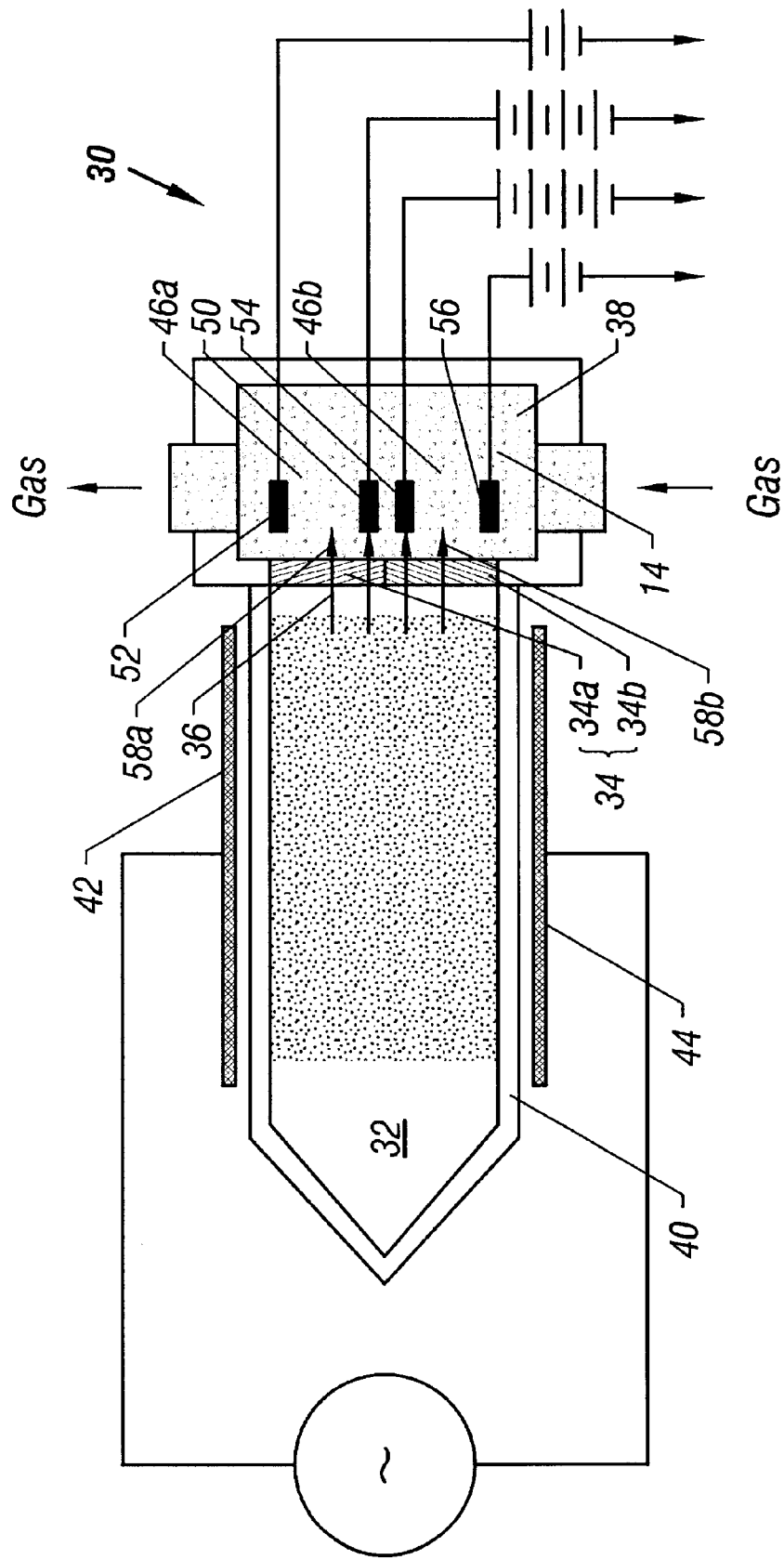
FIG. 2 is a block diagram of a two-channel PID in accordance with an embodiment the present invention.

FIG. 2 illustrates a two-channel photo-ionization detector (PID) 30 in accordance with an embodiment of the present invention. PID 30 includes a UV lamp 32 that produces UV photons or UV light 36 having wavelengths in a range from about 100 to about 200 nm. An optical window 34 of UV lamp 32 has two separate window zones 34a and 34b, and an ionization chamber 38 encloses two corresponding ion detectors 46a and 46b. When a sample containing one or more volatile gases flows through ionization chamber 38, UV light 36 from UV lamp 32 that passes through optical window 34 can ionize the volatile gases, and ion detectors 46a and 46b measure the currents caused by the ionized gas.

UV lamp 32 includes a sealed envelope 40, typically made of glass. Illustrative dimensions for envelope 40 include a diameter of 0.10–1.00 inch, and a length of 0.20–2.00 inches in an exemplary embodiment of the invention. Envelope 40 is between two driver electrodes 42 and 44, which in the exemplary embodiment are metal plates about 0.20 by 0.20 inches. A lamp driver circuit (not shown) applies a high voltage AC signal to electrodes 42 and 44. A lamp driver circuit for generating the high voltage AC signal across driver electrodes 42 and 44 is disclosed in U.S. Pat. No. 5,773,833, which is incorporated herein by reference in its entirety.

The high voltage AC signal on electrodes 42 and 44 induces and maintains glow discharge in gases sealed in envelope 40. The glow discharge produces UV light having a spectrum that depends on the gases in envelope 40 and preferably provides a relatively rich spectrum of UV light. In the exemplary embodiment, envelope 40 contains a mixture of inert gases, for instance, a mixture of 25% helium, 25% argon, 25% krypton and 25% xenon, at a reduced pressure (e.g., 25 Torr).

Optical window 34, which is at an end of envelope 40, has two halves that correspond to window zones 34a or 34b. Each half is made of a different single crystal material. For example, each half of optical window 34 may be made of lithium fluoride (LiF), magnesium fluoride ($MgF_2$), calcium fluoride ($CaF_2$), or barium fluoride ($BaF_2$). Crystalline lithium fluoride (LiF), magnesium fluoride ($MgF_2$), calcium fluoride ($CaF_2$), and barium fluoride ($BaF_2$) respectively transmit UV photons having energies below 11.7 electron volts (eV), 10.6 eV, 9.8 eV, and 9.2 eV. As a result of using different materials, the energy distribution of UV light 36 from zone 34a differs from the energy distribution of UV light 36 from zone 34b. For instance, when zones 34a and 34b are respectively made of LiF and $CaF_2$, UV light 36 from zone 34a has photon energies up to 11.7 eV, and UV light 36 through zone 34b has photon energies up to 9.8 eV.

As described above, ion detectors 46a and 46b in ionization chamber 38 measure currents by collecting the electrons and ions that result from the photo-ionization of gases. Each of ion detector 46a or 46b includes a pair of electrodes for measuring ionization that UV lights from respective window zones 34a and 34b cause. Ion detector 46a includes a bias electrode 50 and a measurement electrode 52, and ion detector 46b includes a bias electrode 54 and a measurement electrode 56. Electrodes 50, 52, 54, and 56 can be made, for example, by machining a sheet of metal, preferably stainless steel. Alternatively, depositing a conductive layer on a substrate and etching the conductive layer can form inter-digital electrodes, and the substrate can be partly removed so as to form a gas flow channel that matches the interdigital electrodes. Exemplary combinations of the electrode layer and the substrate are platinum on a ceramic substrate, copper on a printed circuit board, and gold on a silicon substrate. U.S. patent application Ser. No. 09/177,669, filed Oct. 22, 1998, entitled "A PHOTO-IONIZATION DETECTOR FOR VOLATILE GAS MEASUREMENT AND A METHOD FOR SELF-CLEANING", and U.S. patent application Ser. No. 09/271,612, filed Mar. 17, 1999, entitled "DUAL-CHANNEL PHOTO-IONIZATION DETECTOR THAT ELIMINATES THE EFFECT OF ULTRAVIOLET INTENSITY ON CONCENTRATION MEASUREMENTS", which are herein incorporated by reference in their entireties, further describe ion detectors and their use.

In an exemplary embodiment, electrodes 50, 52, 54 and 56 are about 0.01–0.20 inches, preferably about 0.02 inches, in thickness, and about 0.01–0.08 inches, preferably about 0.02 inches, in width. The distance or separation between bias electrodes 50 or 54 and measurement electrodes 52 or 56 is about 0.01–0.20 inches, preferably about 0.10 inches. These measurements are illustrative in nature, and electrodes 50, 52, 54 and 56 can have other thicknesses, widths, and separations.

To reduce photo-electrons that cause error in the measurement currents, a UV shield (not shown) may be positioned between optical windows 34 and measurement electrodes 52 and 56 to prevent UV light 36 from striking measurement electrodes 52 and 56. For example, a Teflon sheet can be used for the UV shield. Alternatively, as a UV shield, an insulating material layer that is inert to the gases and the ions generated in ionization chamber 38 and opaque to UV light 36 may be formed on surfaces of measurement electrodes 52 and 56 that face optical window 34. For example, a photo-resist polymer such as polytetrafluoroethene (Teflon) or a ceramic such as alumina on the surfaces of measurement electrodes 52 and 56 can serve as a UV shield. The above-described UV shield may also shield bias electrodes 50 and 54.

The energies of UV light 36 from window zone 34a predominantly pass through a region 58a of ionization chamber 38, and UV light 36 from window zone 34b predominantly pass through a region 58b of ionization chamber 38. Accordingly, the energy distribution or spectrum of UV light in region 58a of ionization chamber 38 differs from the spectrum of UV light in region 58b of ionization chamber 38. Some volatile gases that have lower ionization energies can be ionized in both regions 58a and 58b. However, assuming that the maximum energy of UV photons is higher for region 58a than for region 58b, other volatile gases having higher ionization potentials may be ionized only in region 58a, not in region 58b.

Ion detectors 46a and 46b are in regions 58a and 58b respectively and measure currents caused by ionization in the respective regions. These currents depend on the concentration of the ionizable gases in chamber 38 and the intensity of the UV light in each region. Each detector 46a and 46b can be calibrated according to the intensities in respective regions 58a and 58b, so that the concentrations of ionizable gases can be determined from the currents.

In operation, the difference between the concentration determined for region 58a and the concentration determined for region 58b indicates the concentration of gases having ionization potentials between the maximum photon energy for UV light in region 58b and the maximum photon energy for UV light in region 58a. The materials of window zones 34a and 34b can be selected so that a particular gas suspected to be found in a gas sample can be distinguished from other gases that might be found in the gas sample.

Figure 3:
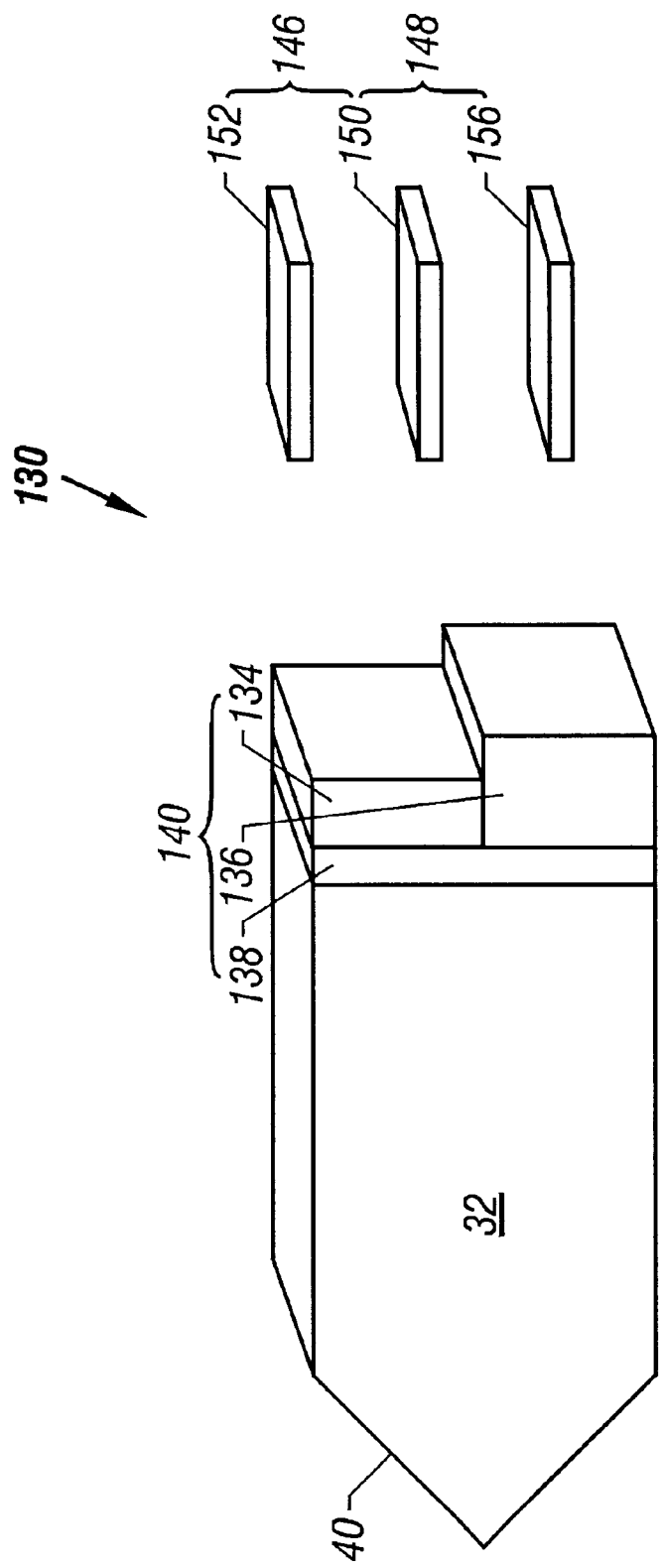
FIG. 3 is a perspective drawing of a two-channel PID in accordance with another embodiment of the invention.

FIG. 3 illustrates another two-channel PID 130 in accordance with an embodiment of the invention. PID 130 includes a UV lamp 32 having a rectangular cross-section, an optical window assembly 140, two ion detectors 146 and 148, and an ionization chamber (not shown)which contains ion detectors 146 and 148. Optical window assembly 140 includes a parent window 138 sealing an envelope 40 of UV lamp 32, and two adjacent area windows 134 and 136 which are attached to parent window 138. Area windows 134 and 136 can be permanently attached to parent window 138 by a glue, or can be detachable from parent window 138 so that area windows 134 and 136 can be replaced. Clips or other structures mechanically attach detachable area windows 134 and 136 to parent window 138. Alternatively, windows assembly 140 can be a single staircase piece. Ion detectors 146 and 148 have measurement electrodes 152 and 156 and a common bias electrode 150. Alternatively, bias electrode 150 can be separated into two bias electrodes like bias electrodes 50 and 54 of FIG. 2. The rectangular cross-section of UV lamp 32 permits measurement electrodes 152 and 156 to be symmetric and relatively large.

Area window 136 is thicker than area window 134 and made of a material that attenuates higher energy UV light. Thus, when UV light from UV lamp 32 passes through optical window assembly 140, area window 134 transmits more UV light having higher energies than area window 136 transmits. For example, a 0.04" thick $MgF_2$ area window may transmit a significant amount of UV light having photon energies up to 10.6 eV, whereas a 0.08" thick $MgF_2$ area window may transmit the UV light lacking photons having energies above 10.3 eV. Accordingly, volatile gas molecules that are ionized in front of area window 134 may not be ionized in front of area window 136. Ion detector 146 measures current produced by the ionized gases near window 134, and ion detector 148 measures current produced by the ionized gases near window 136. The difference in the two measurement currents depends on the concentration of gases having ionization potentials in the range between the maximum photon energy form area window 134 and the maximum photon energy from area window 136.

Two-channel PID 130 of FIG. 3 can identify a concentration for a particular gas or class of gases in the same manner that two-channel PID 30 of FIG. 2 identifies a concentration. However, a PID having more channels can identify concentrations for more types of classes of gases.

Figure 4:
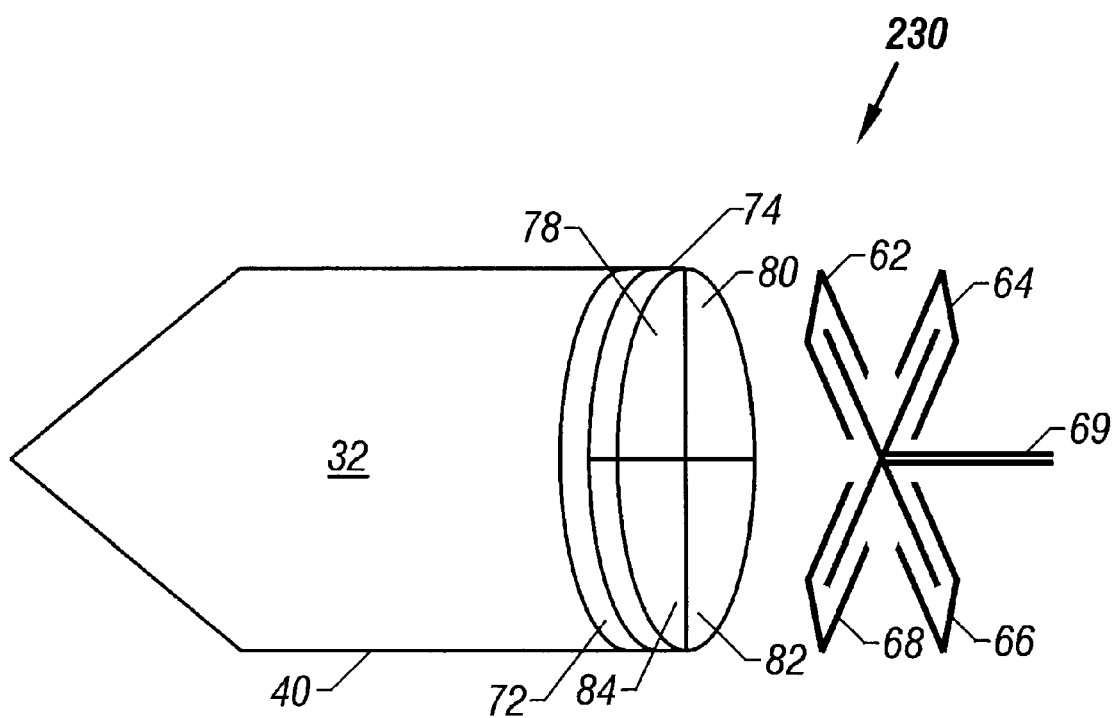
FIG. 4 is a perspective drawing of a four-channel PID in accordance with another embodiment of the invention.

FIG. 4 shows a four-channel PID 230 in accordance with an embodiment of the invention. PID 230 includes a UV lamp 32 having a circular cross-section, an optical window assembly 74, a common bias electrode 69, and measurement electrodes 62, 64, 66, and 68. An ionization chamber (not shown) contains bias electrode 69 and measurement electrodes 62, 64, 66, and 68. Bias electrode 69 can be integrated in a gas inlet or outlet (not shown) of the ionization chamber so that gas flows symmetrically by measurement electrodes 62, 64, 66, and 68.

Optical window assembly 74 includes a parent window 72 for sealing an envelope 40 of UV lamp 32, and four adjacent area windows 78, 80, 82, and 84 which are attached to parent window 72. Parent window 72 transmits UV photons having the same or a higher energy than the highest energy UV photons that area windows 78, 80, 82, and 84 transmit. Area windows 78, 80, 82, and 84 transmit UV lights of different energy levels. In an exemplary optical window assembly, parent window 72 is LiF single crystal, area window 78 is $BaF_2$, area window 80 is $CaF_2$, area window 82 is $MgF_2$, and area window 82 is LiF.

Measurement electrodes 62, 64, 66 and 68 are positioned close to and centered in area windows 78, 80, 82 and 84, respectively. The UV light through each of area windows 78, 80, 82 and 84 selectively ionizes volatile gas molecules in the ionization chamber, making the currents at measurement electrodes 62, 64, 66 and 68 differ from one another. Four-channel PID 230 has more measurement channels and associated UV light beams than does two-channel PIDs 30 and 130 of FIGS. 2 and 3. Accordingly, PID 230 can distinguish among more ionization potentials than the two-channel PIDs 30 and 130 can.

Figure 5:
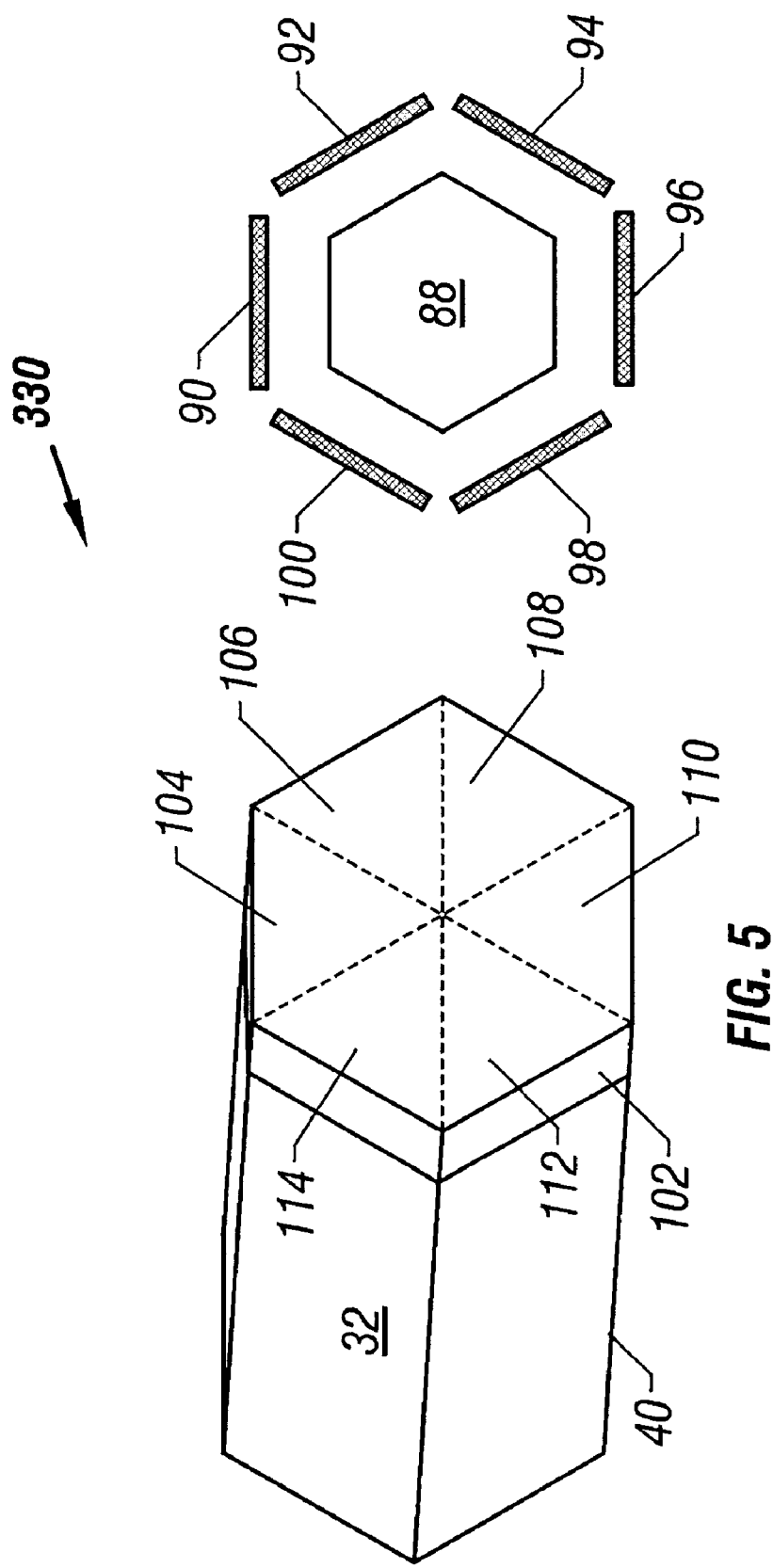
FIG. 5 is a perspective drawing of a six-channel PID in accordance with another embodiment of the invention.

FIG. 5 shows a six-channel PID 330 in accordance with an embodiment of the invention. PID 330 includes a UV lamp 32 having a hexagonal cross-section, an optical window 102 sealing an envelope 40 of UV lamp 32, a common bias electrode 88, and six measurement electrodes 90, 92, 94, 96, 98, and 100. An ionization chamber (not shown) contains bias electrode 88 and measurement electrodes 90, 92, 94, 96, 98, and 100 for exposure to a gas being analyzed. Optical window 102 includes six window zones 104, 106, 108, 110, 112, and 114, each of which transmits UV light having different energy spectrum.

Six window zones 104, 106, 108, 110, 112, and 114 of optical window 102 can be formed by partly modifying a single crystal sheet that forms optical window 102. For example, differentiated thermal diffusion, ion implantation, or plasma treatment can materially modify a single crystal sheet made of LiF, $MgF_2$, $CaF_2$, $BaF_2$, fused quartz or a UV-transmitting glass and produce six window zones 104, 106, 108, 110, 112, and 114 having different properties for transmission of UV light. Alternatively, fusing or gluing of six triangular single crystal pieces can form optical window 102.

Bias electrode 88 is centered on the central axis of UV lamp 32, and can be integrated in a gas inlet or outlet (not shown) of the ionization chamber. Measurement electrodes 90, 92, 94, 96, 98 and 100 are symmetrically disposed near window zones 104, 106, 108, 110, 112 and 114, respectively. The UV light through window zones 104, 106, 108, 110, 112 and 114 selectively ionize volatile gas molecules in the ionization chamber, making currents from bias electrode 88 to measurement electrodes 90, 92, 94, 96, 98 and 100. The currents at measurement electrodes 90, 92, 94, 96, 98 and 100 depend on the energy spectrums of the UV light from the associated window zones 104, 106, 108, 110, 112 and 114.

A PID in accordance with other embodiments of the invention can have any desired number of differentiated areas (window zones). FIG. 5 illustrates an embodiment with a hexagonal cross-section and six-way symmetry. In general, a lamp having a cross-section that is an N-sided equal-lateral polygon or a circle can include N different triangular or pie-piece shaped zones. An N-sided bias electrode with N measurement electrodes parallel to the sides of the bias electrode can provide N symmetric measurement channels. More channels provide better selective ionization and measurement of particular volatile gases.

Multi-channel PIDs 30, 130, 230, and 330 allow determination of the concentrations of volatile gases having specific ionization potentials and identification of specific gases.

Figure 6:
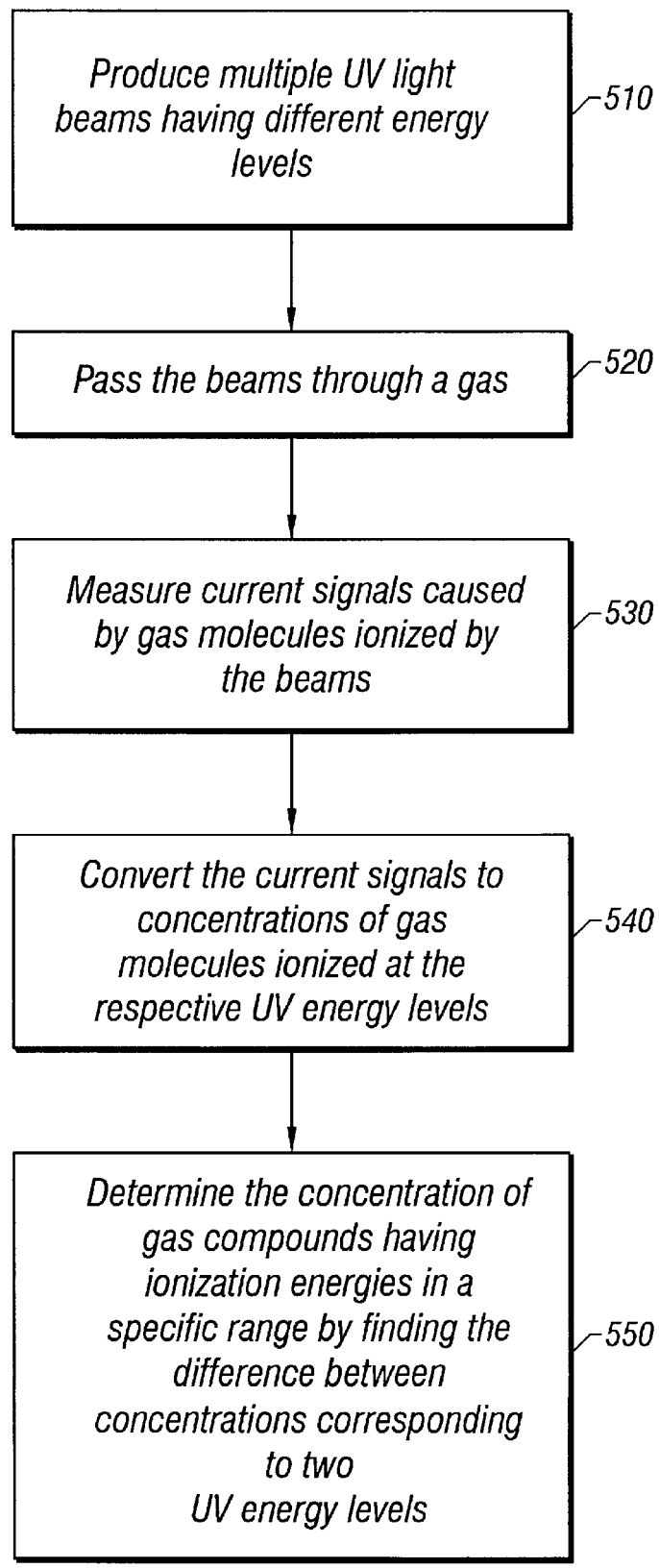
FIG. 6 is a flowchart of a method for determining the concentrations of individual component gases in a gas sample in accordance with another embodiment of the invention.

FIG. 6 illustrates a method for determining the concentration of gases having ionization energies in a specified range. In step 510, multiple window zones $Z_1$ to $Z_N$ of an optical window produce N UV light beams $UV_1$ to $UV_N$ having maximum photon energies $E_1$ to $E_N$ in order of increasing maximum photon energy. In step 520, UV light beams $UV_1$ to $UV_N$ ionize volatile gases in a gas sample. Different gases may be ionized in areas corresponding to multiple window zones $Z_1$ to $Z_N$. In step 530, separate ion detectors measure current signals $S_1$ to $S_N$ corresponding to zones $Z_1$ to $Z_N$. Step 540 converts current signals $S_1$ to $S_N$ into concentrations $C_1$ to $C_N$ of ionizable gases. The conversion can be performed using a conversion table calibrated according to current signals measured for sample gases of known concentrations. Finally, in step 550, the difference between consecutive concentrations $C_i$ and $C_{i+1}$ determines the concentration of gases having ionization potential between the maximum energies $E_i$ and $E_{i+1}$. That is, step 550 determines the concentration of gases that are ionized by the UV light of photon energy $E_{i+1}$ or less, but not ionized gases by the UV light of photon energy $E_i$ or less.

Using the method of FIG. 6, the presence of one of more suspected gases can be detected by choosing photon energies $UV_1$ to $UV_N$ to distinguish one suspected gas from another. For example, in order to measure benzene (ionization potential=9.25 eV) from toluene (ionization potential=8.82 eV) background, energy $E_i$ is set just below 9.25 eV (e.g., 9.0 eV), and energy $E_{i+1}$ is set above 9.25 eV (e.g., 9.6 eV). The range between $E_i$ and $E_{i+1}$ are set such that ionization potentials of other suspected gases, such as toluene, do not fall within the range. As described above in step 550 of FIG. 6, the difference between consecutive concentrations $C_i$ and $C_{i+1}$ at energies $E_i$ and $E_{i+1}$ determines the concentration of ionizable gas, likely to be benzene.

Figure 7:
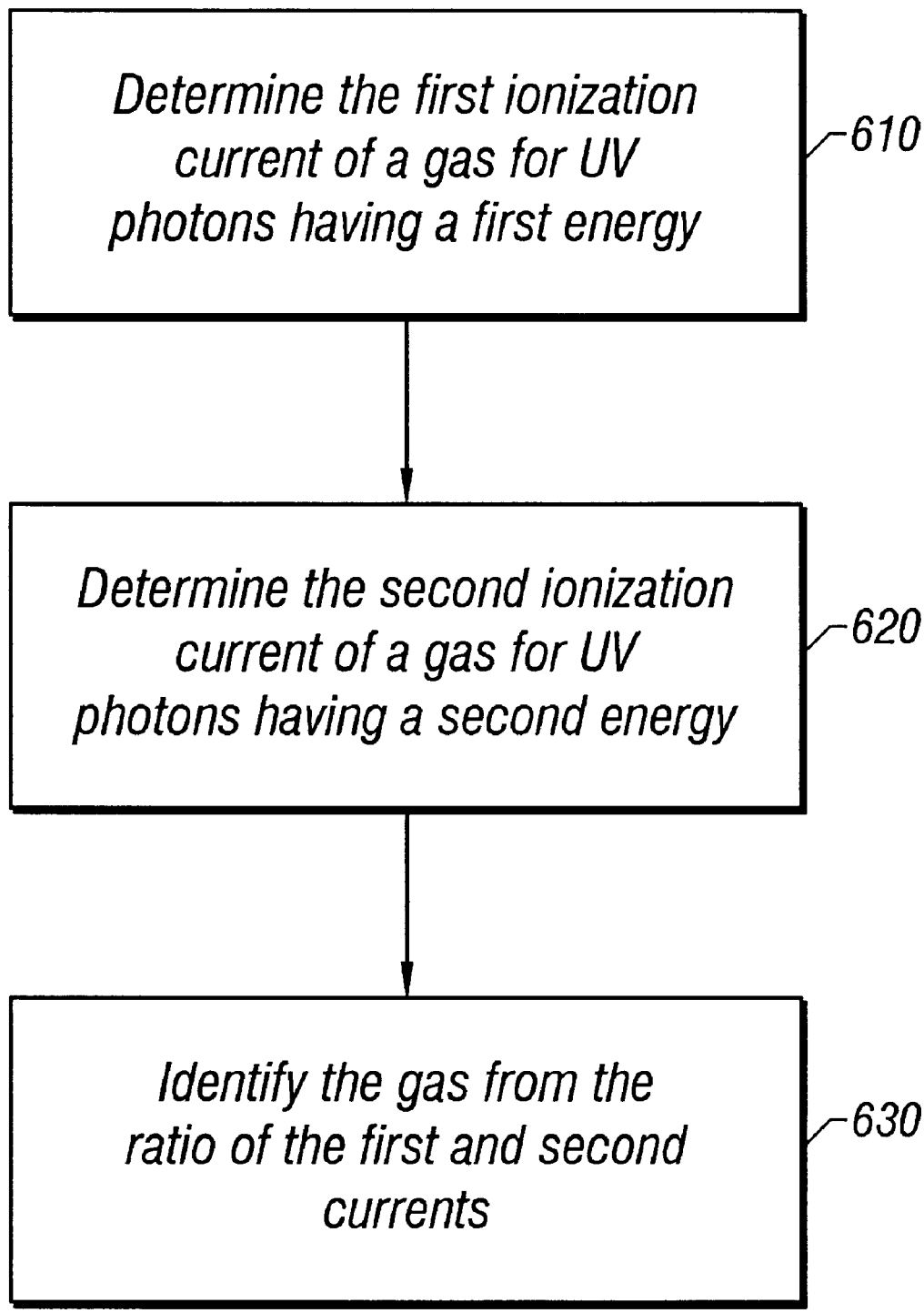
FIG. 7 is a flowchart of a method for identifying a gas included in a gas sample in accordance with another embodiment of the invention.

FIG. 7 illustrates another method for determining the concentration and chemical identification of a volatile gas. As explained above, if only one kind of suspected gas has ionization potential between photon energies $E_i$ and $E_{i+1}$, the process of FIG. 6 can identify the gas by determining the concentrations of all gases having ionization potential between photon energies $E_i$ and $E_{i+1}$. However, two different suspected gases may have ionization potentials between photon energies $E_i$ and $E_{i+1}$. In this case, the two gases may be distinguished by measuring concentration (or, ionization) ratios of volatile gases at different energy levels, and comparing the measured ratios to a table of ratios for suspected gases.

In distinguishing or identifying a particular gas having ionization potentials between photon energies $E_i$ and $E_{i+1}$, step 610 determines an current $I_i$ associated with beam $UV_{i+1}$ which has maximum photon energy $E_{i+1}$. Step 620 determines an ionization current $I_j$ associated with a UV light beam $UV_j$, which has a maximum energy $E_j$ that is greater than energy $E_{i+1}$. Then, in step 630, the gas is identified by comparing the ratio $I_i/I_j$ to a table of ratios for suspected gases. For example, n-butanol and isobutanol have almost the same level of ionization at UV photons having maximum energy of 10.6 eV. But they have different degrees of ionization at UV photons having maximum energy of 10.0 eV. That is, the ratios of ionization by maximum UV photon energies of 10.0 eV and 10.6 eV are 0.07:1.00 for n-butanol and 0.20:1.00 for isobutanol.

Although the invention has been described with reference to particular embodiments, the description is only an example of the inventor's application and should not be taken as a limitation. For example, the identification between the gases as described above can use either the measured concentrations or currents since the two are directly related to each other. Various other adaptations and combinations of features of the embodiments disclosed are within the scope of the invention as defined by the following claims.

We claim:

1. A photo-ionization detector comprising:
 a UV light source;
 an optical window having a plurality of window zones, one of the window zones transmitting UV light having a first energy spectrum, which is different from a second energy spectrum of UV light transmitted from another one of the window zones;
 an ionization chamber adjacent to the optical window; and
 a plurality of ion detectors in the ionization chamber, each of the ion detectors measuring ionization that UV light from a corresponding one of the window zones causes.

2. The photo-ionization detector of claim 1, wherein the optical window comprises:
 a parent window; and
 a plurality of area windows attached to the parent window to form the window zones.

3. The photo-ionization detector of claim 2, wherein a first thickness of one of the area windows differs from a second thickness of another one of the area windows.

4. The photo-ionization detector of claim 2, wherein the area windows are permanently attached to the parent window.

5. The photo-ionization detector of claim 2, wherein the area windows are detachable from the parent window so that the area windows can be replaced.

6. The photo-ionization detector of claim 2, wherein one of the area windows is made of a material having UV light-transmitting characteristics that differ from UV light-transmitting characteristics of another one of the area windows.

7. The photo-ionization detector of claim 2, wherein the material of each of the area windows is selected from a group consisting of lithium fluoride (LiF), magnesium fluoride ($MgF_2$), calcium fluoride ($CaF_2$), barium fluoride ($BaF_2$), fused quartz, and a UV-transmitting glass.

8. The photo-ionization detector of claim 1, wherein the optical window comprises a single material having modified areas that form the window zones.

9. The photo-ionization detector of claim 8, wherein a first thickness of one of the modified areas differs from a second thickness of another one of the modified areas.

10. The photo-ionization detector of claim 8, wherein one of the modified areas differs in UV light-transmitting characteristics from another one of the modified areas.

11. The photo-ionization detector of claim 10, wherein one of the modified areas differs in impurity content from another one of the modified areas.

12. The photo-ionization detector of claim 1, wherein each of the ion detectors comprises:
   a first electrode electrically biased to attract positively charged particles; and
   a second electrode electrically biased to attract negatively charged particles.

13. The photo-ionization detector of claim 12, wherein the second electrodes are integrated into a common electrode.

14. The photo-ionization detector of claim 1, further comprising a UV shield between the optical window and the ion detectors.

15. The photo-ionization detector of claim 1, wherein the ion detectors are close to the corresponding window zones of the optical window.

16. A method for determining a concentration of selected gas compounds in a gas, comprising:
   producing a plurality of UV light beams, wherein a first energy spectrum of one of the UV light beams differs from a second energy spectrum of another one of the UV light beams;
   passing the UV light beams through the gas;
   measuring a plurality of current signals caused by the UV light beams ionizing gas molecules; and
   determining the concentration of the selected gas compounds from a difference in measurements.

17. The method of claim 16, wherein determining the concentration comprises:
   converting the current signals to concentrations of gas molecules ionizable by each of the UV light beams; and
   determining the concentration of the selected gas compounds by finding a difference between a first concentration of gas molecules ionizable by a first UV light beam and a second concentration of gas molecules ionizable by a second UV light beam.

18. The method of claim 16, wherein producing the UV lights comprises passing UV light through a energy screening medium that separates the UV light into the UV light beams.

19. A method for identifying a gas in a sample, comprising:
   producing a plurality of UV light beams, wherein a first energy spectrum of one of the UV light beams differs from a second energy spectrum of another one of the UV light beams;
   passing the UV light beams through the sample;
   measuring current signals caused by ionization of the sample associated with respective UV light beams; and
   comparing a ratio derived from the current signals to a ratio associated with the gas.

20. The method of claim 19, wherein producing the UV lights beams comprises passing UV light through a screening medium to separate the UV light into the UV light beams.

* * * * *